United States Patent
Safai et al.

(10) Patent No.: US 9,664,616 B2
(45) Date of Patent: May 30, 2017

(54) METHODS AND SYSTEMS FOR NON-DESTRUCTIVE TESTING VIA HYBRID SPECTRAL SENSORS

(71) Applicant: The Boeing Company, Chicago, IL (US)

(72) Inventors: Morteza Safai, Newcastle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/932,582

(22) Filed: Nov. 4, 2015

(65) Prior Publication Data
US 2017/0122866 A1 May 4, 2017

(51) Int. Cl.
*G01N 21/64* (2006.01)

(52) U.S. Cl.
CPC .................................. *G01N 21/64* (2013.01)

(58) Field of Classification Search
CPC .............................. G01N 21/64; G01N 31/00
USPC ....................................................... 250/459.1
See application file for complete search history.

(56) References Cited

U.S. PATENT DOCUMENTS

| | | | |
|---|---|---|---|
| 5,483,338 A | 1/1996 | Wachter et al. | |
| 7,902,524 B2 * | 3/2011 | Safai | B82Y 15/00 250/458.1 |
| 8,185,326 B2 | 5/2012 | Safai et al. | |
| 2002/0021003 A1 * | 2/2002 | McGrew | B41M 3/144 283/93 |
| 2003/0066998 A1 * | 4/2003 | Lee | B82Y 10/00 257/19 |
| 2003/0218143 A1 * | 11/2003 | Shields | B82Y 20/00 250/493.1 |

(Continued)

FOREIGN PATENT DOCUMENTS

| | | |
|---|---|---|
| GB | 2194062 A | 2/1988 |
| JP | 5556973 B2 | 7/2014 |

OTHER PUBLICATIONS

"Prepreg Compositions, Their Manufacture, and Determination of Their Suitability for Use in Composite Structures", U.S. Appl. No. 14/503,201, filed Sep. 30, 2014, 40 pgs.

(Continued)

*Primary Examiner* — Casey Bryant
(74) *Attorney, Agent, or Firm* — Kwan & Olynick LLP

(57) ABSTRACT

Provided are methods and systems for non-destructive testing of parts while these parts are being fabricated and/or operated. A part has hybrid spectral sensors embedded within and bonded to one or more other components of the part. A hybrid spectral sensor may include two different structures. A first structure of the sensor provides a first spectral response when exposed to an excitation radiation. A second structure forms a Faraday cage around the first structure and blocks the excitation radiation to the first structure and/or blocks the first spectral response emitted by the first structure if the first structures gets exposed to the excitation radiation. The second structure may be bonded to one or more components of the part, such as a matrix resin, and may change its coverage of the first structure during fabrication and/or operation of the part thereby altering its blocking characteristics.

18 Claims, 12 Drawing Sheets

(56) References Cited

U.S. PATENT DOCUMENTS

| | | | |
|---|---|---|---|
| 2004/0055699 A1* | 3/2004 | Smith | B29C 65/344 156/273.9 |
| 2005/0139753 A1* | 6/2005 | Park | H01L 31/02161 250/214.1 |
| 2005/0272856 A1* | 12/2005 | Cooper | B82Y 30/00 524/496 |
| 2006/0273249 A1* | 12/2006 | Webster | H01L 27/14618 250/239 |
| 2007/0223097 A1* | 9/2007 | Garware | B32B 7/12 359/586 |
| 2008/0312847 A1 | 12/2008 | Safai et al. | |
| 2010/0015462 A1* | 1/2010 | Jablonski | B22F 7/04 428/553 |
| 2010/0151577 A1* | 6/2010 | Davis | B82Y 15/00 436/6 |
| 2010/0213387 A1 | 8/2010 | Safai et al. | |
| 2012/0162641 A1* | 6/2012 | Schmidt | G01J 3/28 356/301 |
| 2013/0079611 A1* | 3/2013 | Besko | A61B 5/14552 600/344 |
| 2015/0140562 A1* | 5/2015 | Conoci | G01N 21/6452 435/6.11 |

OTHER PUBLICATIONS

Zhao, Haiguang et al., "Investigating photoinduced charge transfer in double- and single-emission PbS@CdS core@shell quantum dots", Nanoscale, 6, 2014, pp. 215-225.

"European Application Serial No. 16195722.0, Search Report mailed Mar. 17, 2017", 10 pgs.

* cited by examiner

*For Example,
Plasma Ionic
Aggregation of
Different Structures*

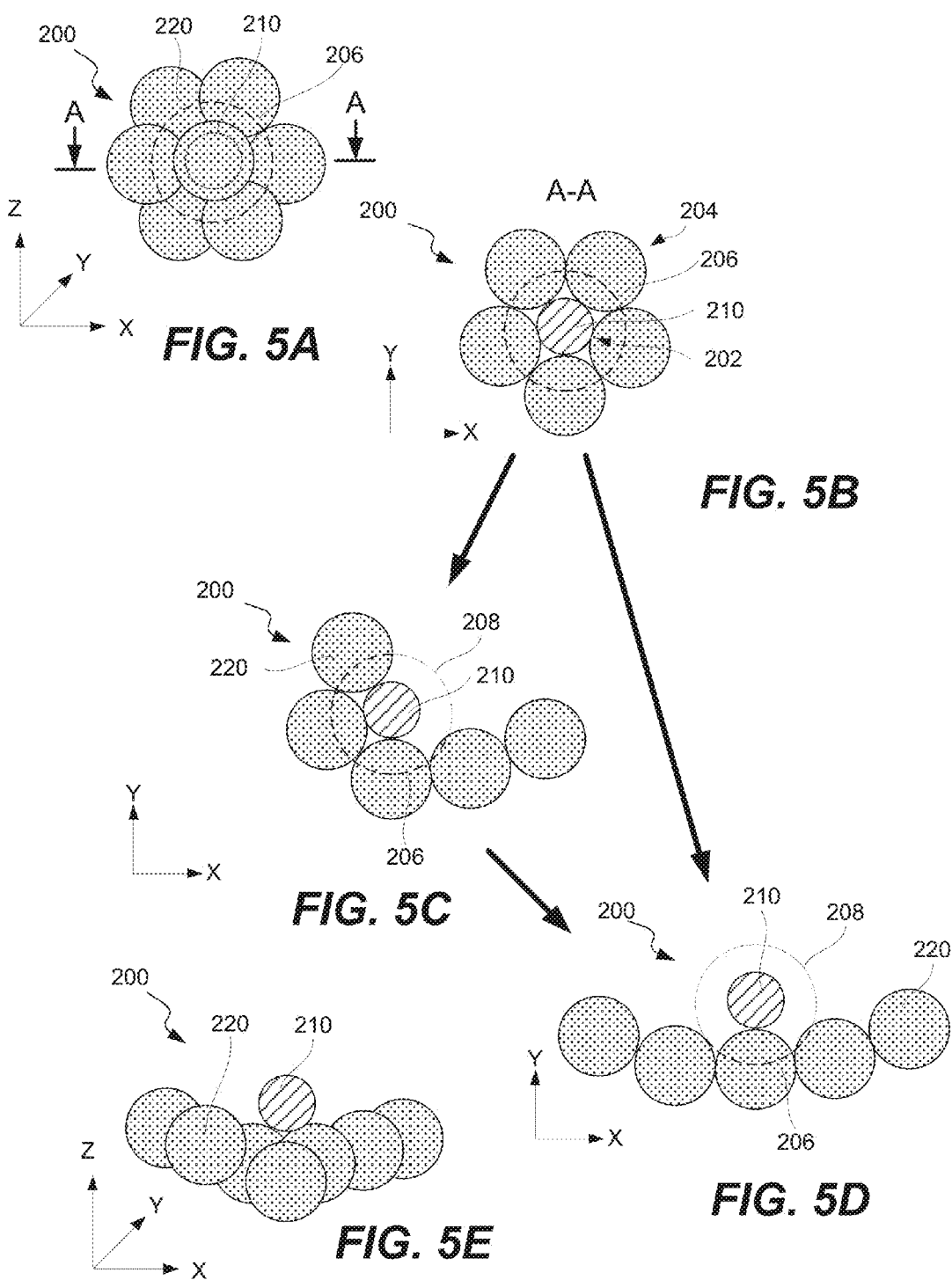

METHODS AND SYSTEMS FOR NON-DESTRUCTIVE TESTING VIA HYBRID SPECTRAL SENSORS

BACKGROUND

To verify structural integrity or other characteristics of parts, such as bond lines of composite structures, various destructive and non-destructive inspection techniques have been proposed. However, most of the current techniques have limitations. For example, destructive inspection techniques cannot be used on actual production parts and may provide only limited characterization during process development and quality control. Non-destructive inspection techniques include various ultrasonic methods. However, these currently available methods facilitate less than desired verification of bond strength throughout the life cycle of a bond. One example of ultrasonic inspection involves detecting and analyzing attenuation through part-adhesive interfaces. Another example involves detecting and analyzing reflections from part-adhesive interfaces. Yet another example involves ultrasonic resonance, where changes in resonance frequencies are monitored to indicate flaws. What is needed is a method and device which allows verifying directly that the required bondline properties have been achieved.

SUMMARY

Provided are methods and systems for non-destructive testing of parts while these parts are being fabricated and/or used in operation. A tested part includes hybrid spectral sensors embedded within the part and bonded to one or more other components of the part. A hybrid spectral sensor may include two different structures. A first structure of the sensor provides a first spectral response when exposed to an excitation radiation. A second structure forms a Faraday cage around the first structure and blocks the excitation radiation to the first structure and/or blocks the first spectral response emitted by the first structure (if the first structures gets exposed to the excitation radiation). The second structure may be bonded to one or more components of the part, such as a matrix resin, and may change its encapsulation level of the first structure and its blocking characteristics when the part is subjected to one or more operations. These changes in the hybrid spectral sensors may be detected by exposing the part to the excitation radiation. Furthermore, these blocking characteristics may be correlated to various structural integrity characteristics of the part. The hybrid spectral sensors remain in the part and may be retested multiple different times during fabrication and/or operation of the part.

In some embodiments, a method comprises forming a Faraday cage around a first structure by at least partially encapsulating the first structure with at least one second structure to form a hybrid spectral sensor. As such, the hybrid spectral sensor includes the first structure at least partially encapsulated by the at least one second structure. The level of encapsulation defines the blocking characteristics of the Faraday cage in the hybrid spectral sensor. The method may also comprise incorporating the hybrid spectral sensor into the part.

In some embodiments, encapsulating the first structure with the at least one second structure comprises plasma ionic aggregation. After encapsulating the first structure with the at least one second structure, the first structure may be cohesively bonded to the at least one second structure. When multiple second structures are used within the same hybrid spectral sensor, each of these second structures may be independently cohesively bonded to the first structure or to one of multiple first structures of the same hybrid spectral sensor.

In some embodiments, the least one second structure is also bonded to a component of the part after the hybrid spectral sensor is incorporated into the part. This component may be an adhesive. Different portions of the least one second structure of the same hybrid spectral sensor or different second structures of the same hybrid spectral sensor may be bonded to different portions of the component. The bond between the least one second structure and the component may be stronger than the bond between the least one second structure and the first structure.

In some embodiments, the first structure is a first quantum dot. The at least one second structure may be a second quantum dot different from the first quantum dot. When multiple second structures are used for the same hybrid spectral sensor, all second structures may be the same type. When exposed to the same excitation radiation, the first quantum dot produces a different excitation radiation than the second quantum dot. Furthermore, the second quantum dot may block the excitation radiation to the first quantum dot.

In some embodiments, the Faraday cage is configured to block at least one of the excitation radiation to the first structure or the emitted radiation from the first structure. More specifically, the Faraday cage may be configured to block both the excitation radiation to the first structure and the emitted radiation from the first structure.

In some embodiments, the part is a composite part. The hybrid spectral sensor may incorporated into any one or all of plies forming a layup, into an adhesive used between the plies and/or to form the plies, and other purposes. When the part is a composite part, the method may comprise curing the part. The hybrid spectral sensor may be incorporated into the part prior to curing the part. Furthermore, the hybrid spectral sensor may be used to monitor changes in the part during the curing operation.

In some embodiments, the method further comprises exposing the part to an excitation radiation and analyzing spectrum of an emitted radiation from the part to determine inconsistencies in the part. The emitted radiation may be emitted from the part or, more specifically, from the hybrid spectral sensors incorporated into the part as a result of the part being exposed to the excitation radiation. The spectrum of the emitted radiation depends on openings in the Faraday cage of the hybrid spectral sensor, which in turn affect the blocking characteristics of the Faraday cage. In other words, the spectrum of the emitted radiation depends on the level of encapsulation of the first structure with the at least one second structure. This level of encapsulation may change as the part is processed and/or used.

The portion of the emitted radiation attributable to the first structures is distinguishable from the portion of the emitted radiation attributable to the at least one second structure, if there is anything emitted from the at least one second structure. In some embodiments, the at least one second structure does not produce any detectable emitted radiation when exposure to the emitted radiation. The distinction in the emitted radiation may come from different materials used for the first structure and the second structure.

In some embodiments, the method further comprises processing the part. This processing may be performed prior to exposing the part to the excitation radiation and after incorporating the hybrid spectral sensor into the part. As such, processing may be followed by exposing the part to the excitation radiation. In some embodiments, additional exposure to the same or similar excitation radiation may be performed prior to processing. The processing may comprise bondline curing.

In some embodiments, the method further comprises processing the part after exposing the part to the excitation radiation and then exposing the part to an additional excitation radiation (after completing the processing). The method may proceed with analyzing the spectrum of an additional emitted radiation. The method may further comprise comparing the spectrum of the emitted radiation to the spectrum of the additional emitted radiation. The difference between the two spectrums may be indicative of changes in the part that occur during processing.

In some embodiments, the Faraday cage is formed by fully encapsulating the first structure with the at least one second structure. This full encapsulation may be achieved prior to incorporating the hybrid spectral sensor into the part. In some embodiments, the first structure is encapsulated by multiple second structures comprising the at least one second structure. In the same of other embodiments, the at least one second structure form an encapsulating shell around the first structure.

Provided also is a method of testing a part. The method may comprises exposing the part to an excitation radiation and analyzing spectrum of an emitted radiation from the part to determine inconsistencies in the part. The part may comprise hybrid spectral sensors.

Each of the hybrid spectral sensors of the part may comprise a Faraday cage around a first structure formed by at least partially encapsulating the first structure with at least one second structure.

In some embodiments, the least one second structure is bonded to a component of the part after the hybrid spectral sensor is incorporated into the part. The component of the part may be an adhesive.

The first structure may be a first quantum dot. The at least one second structure may be a second quantum dot different from the first quantum dot. The first structure may be cohesively bonded to the second structures.

In some embodiments, the Faraday cage is configured to block at least one of an excitation radiation or an emitted radiation from the first structure. More specifically, the Faraday cage is configured to block both the excitation radiation and the emitted radiation from the first structure. The spectrum of the emitted radiation may depend on an opening in the Faraday cage of the hybrid spectral sensor.

In some embodiments, a portion of the emitted radiation attributable to the first structures is distinguishable from a portion of the emitted radiation attributable to the second structures. The second structures may provide substantially no contribution to the emitted radiation, in some embodiments. Alternatively, any contribution to the emitted radiation by the second structures may be ignored during analysis of the spectrum of the emitted radiation.

In some embodiments, the method further comprises processing the part. This processing may be performed prior to exposing the part to the excitation radiation. For example, this processing may comprise bondline curing.

In some embodiments, the method of claim 21 further comprises processing the part after exposing the part to the excitation radiation and exposing the part to an additional excitation radiation after completing the processing. The method may also involve analyzing spectrum of the additional emitted radiation. In some embodiments, the method further comprises comparing the spectrum of the emitted radiation to the spectrum of the additional emitted radiation.

Provided also is a hybrid spectral sensor comprising a first structures and a Faraday cage around a first structure formed by at least partially encapsulating the first structure with at least one second structure. The Faraday cage may be configured to block at least one of an excitation radiation or a portion of an emitted radiation emitted by the first structure. More specifically, the Faraday cage may be configured to block both the excitation radiation and the portion of the emitted radiation emitted by the first structure.

In some embodiments, the first structure is cohesively bonded to the at least second structure. The first structure may be a first quantum dot. The at least one second structure may be a second quantum dot different from the first quantum dot.

Provided also is a part comprising a component and a hybrid spectral sensor. The hybrid spectral sensor may comprise a first structures and a Faraday cage around a first structure formed by at least partially encapsulating the first structure with at least one second structure. The Faraday cage may be configured to block at least one of an excitation radiation or a portion of an emitted radiation emitted by the first structure. More specifically, the Faraday cage is configured to block both the excitation radiation and the portion of the emitted radiation from the first structure.

The first structure may be cohesively bonded to the at least second structure. The first structure may be a first quantum dot. The at least one second structure may be a second quantum dot different from the first quantum dot. The least one second structure may be bonded to the component of the part after the hybrid spectral sensor is incorporated into the part. The component may be an adhesive. The part may be a composite part.

These and other embodiments are described further below with reference to the figures.

BRIEF DESCRIPTION OF THE DRAWINGS

FIGS. 5A-5E are schematic representations of the same hybrid spectral sensor at different states, in accordance with some embodiments.

DETAILED DESCRIPTION

Figure 1:
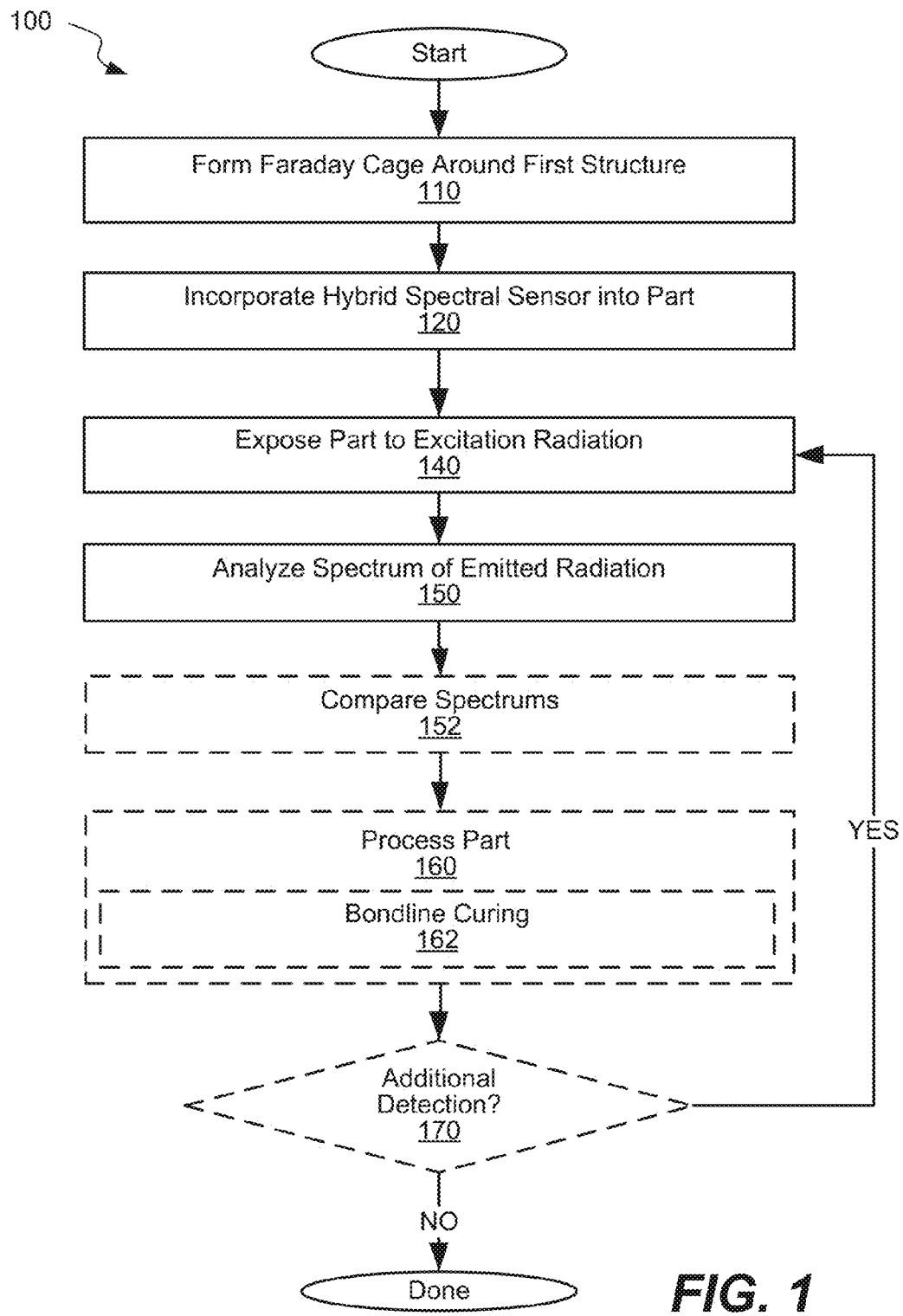
FIG. 1 is a process flowchart corresponding to a method for non-destructive testing of a part, in accordance with some embodiments.

In the following description, numerous specific details are set forth to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

It has been found that incorporating hybrid spectral sensors into parts in particular ways allows detecting various structural changes in these parts that may occur during processing (e.g., fabrication) and/or using (e.g., operation) of these parts. A hybrid spectral sensor used for these parts may include at least one first structure forming a core of the sensor. The first structure may have a distinctive spectral response distinguishable from response of other components of the part, if there are any such responses. The sensor also includes at least one second structure initially forming a Faraday cage around the at least one first structure. The orientation of the at least one second structure relative to the at least one first structure may change due to structural changes within the part. This change in orientation results in changes of blocking characteristics of the Faraday cage and different spectral response from the sensor. Specifically, during incorporation of the sensor into the part, the at least one second structure may be bonded to one or more components of the part, such as an adhesive. This bond may be stronger than the bond between the first and second structures. When the part components move during processing and/or use of the part, they also pull the at least one second structure into a new location thereby changing the relative orientations of the first and second structures. The changes in the blocking characteristics of the Faraday cage and the different spectral responses from the sensor may be monitored with expositing the part to excitation radiation and then analyzing the spectrum of the emitted radiation. One having ordinary skills in the art that the same part may have a plurality of sensors.

In some embodiments, first and second components of a hybrid spectral sensor may be formed two sets of different quantum dots. For purposes of this disclosure, the quantum dots may be also referred to as Q-dots. Specifically, the first set of one or more quantum dots represent the at least one first structure (in the above example) forming a core of the hybrid spectral sensor. These one or more quantum dots may be referred to as inner quantum dots. The second set of one or more quantum dots represent the at least one second structure in the above example forming a shell of the hybrid spectral sensor. These one or more quantum dots may be referred to as outer quantum dots. In this example, a hybrid spectral sensor may be also referred to as a hybrid quantum dot nanotechnology crystal system. Each set of quantum dots provide a different response when exposed to an excitation radiation. Furthermore, the outer quantum dots arranges into the shell create a Faraday cage that may prevent the excitation radiation to reach the inner quantum dots (and to generate any emitted radiation by the inner quantum dots). In another example, the Faraday cage shields the radiation emitted by the inner quantum dots even if the excitation radiations reaches the inner quantum dots. Furthermore, the Faraday cage may be formed to shield the inner quantum dots from the excitation radiation as well as to shield the rest of the system from the radiation emitter from the inner quantum dots (if any excitation radiation reaches the inner quantum dots and causes the emission). The location of the scanner may be also considered because the changes in the blocking properties of the Faraday cages may be directional, e.g., more on side than the other. Furthermore, some premature changes in blocking properties of the Faraday cages may occur. However, the signal attributed to these changes may be minimal and generally ignored. It should be noted that references are often made to multiple first and second structures, one having ordinary skill in the art would understand that any number of first and second structures may be used to form a single hybrid spectral sensor as further described below. Furthermore, one having ordinary skill in the art would understand that different hybrid spectral sensors in the same part may have some variations in the number of first and second structures forming each of these hybrid spectral sensors.

The hybrid spectral sensors may be mixed within a composite resin, bondline adhesive, or any other material of the part prior to curing the part. During the curing process, the shell formed by the second structures (e.g., outer quantum dots) may change. For example, the shell may open up and lose some of its Faraday cage shielding efficiency. If that happens, the hybrid spectral sensors will change their spectral response. Specifically, more excitation radiation may be able to reach the first structures (e.g., inner quantum dots) and/or more emitted radiations may escape from the first structures and reach the detector. Depending on the curing conditions and other factors, the hybrid spectral sensors may experience different changes of their spectral response characteristics, which depend on shielding characteristics of the Faraday cages formed by the second structures. As such, the spectral response may be used as indirect characterization of the curing process and other characteristics (e.g., structural characteristics, structural changes) of the part. For example, by measuring the intensity of the spectrum peak (signal) attributable to the first structures (e.g., inner quantum dots), the quality of bonding process can be evaluated.

The spectral profile of a part having hybrid spectral sensors may be also referred to as an electromagnetic signature of the part. Since the spectral profile changes with changes inside the part, the spectral profile may be used as a characterization of the strength and quality of the bond and ultimately to make a decision if the bond should pass the inspection.

Non-Destructive Testing and Hybrid Spectral Sensor Examples

FIG. 1 is a process flowchart corresponding to method 100 for non-destructive testing of a part, in accordance with some embodiments. Method 100 may commence with forming Faraday cage 206 around first structure 210 (refer to block 110 in FIG. 1). Faraday cage 206 may be formed by at least partially encapsulating first structure 210 with at least one second structure 220. This in turn forms hybrid spectral sensor 200. In other words, when formed, hybrid spectral sensor 200 includes Faraday cage 206. The shielding characteristics of Faraday cage 206 at this stage may be the greatest and may later change as hybrid spectral sensor 200 are subjected to various internal forces within part 300.

Figure 2A:
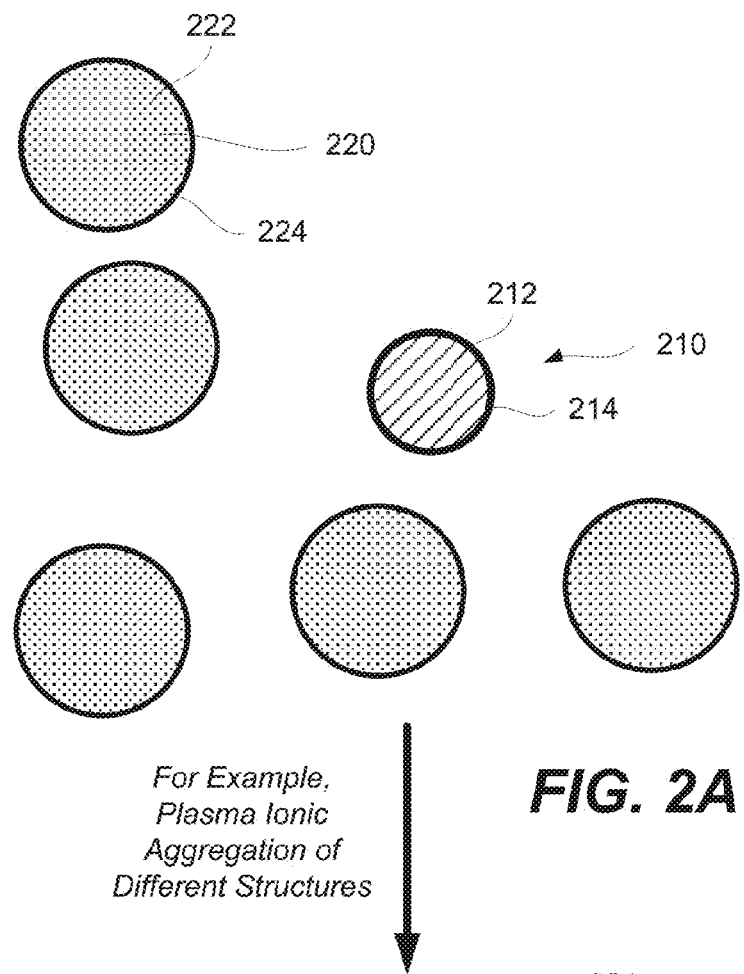
FIGS. 2A and 2B are two schematic representations of different stages while forming a hybrid spectral sensor, in accordance with some embodiments.
Figure 2B:
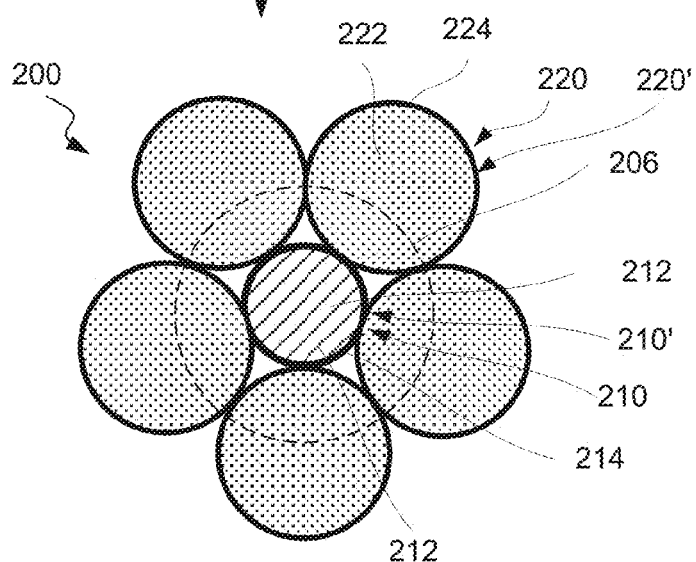

FIG. 2A is a schematic illustration of several second structures 220 and first structure 210 prior to forming Faraday cage 206. FIG. 2B is a schematic illustration of the same second structures 220 forming Faraday cage 206 around first structure 210. The overall assembly shown in FIG. 2B may be referred to as hybrid spectral sensor 200.

While six second structures 220 are shown in FIGS. 2A and 2B, one having ordinary skills in the art would recognize that any number of second structures 220 may be used to form Faraday cage 206 around first structure 210. In some embodiments, single second structure 220 may be used to form Faraday cage 206 as, for example, shown in FIG. 2C. Furthermore, Faraday cage 206 may be formed around multiple first structures 210, which together form a cluster. The number of each of first structures 210 and second structures in each of hybrid spectral sensor 200 may depend on the size of each structure, encapsulation level of Faraday cage 206 needed at least initially, and other factors. It should be noted that the encapsulation level of Faraday cage 206 may change after hybrid spectral sensor 200 is incorporated into a part.

In some embodiments, first structure 210 is first quantum dot 210'. At least one second structure 220 may be second quantum dot 220' different from first quantum dot 220'. In a specific example, first structures 210 forming hybrid spectral sensors are PbS quantum dots, while second structures 220 are CdS quantum dots. A charge transfer may occur between PbS-core quantum dots and CdS-shell quantum dots, such that hybrid spectral sensor 200 may generate either a single emission peak from second structures 220 or a double emission peaks from both first structures 210 and second structures 220. Also, by controlling the quenching of one with respect to the other, the charge transfer between first structures 210 and second structures 220 and their emission peaks can be tuned. Quenching can be used to control the process of decreasing the fluorescence intensity of one quantum-dot relative to the other quantum-dot. These approaches can be used to form custom hybrid spectral sensors. In general, when exposed to the same excitation radiation, first quantum dot 210' produces a different excitation radiation than second quantum dot 220'. Different excitation radiations of first quantum dot 210' and second quantum dot 220' allow to determine shielding characteristics of Faraday cage 206 since the spectrum attributed to first quantum dot 210' may be distinguishable from the spectrum attributed to second quantum dot 220' and the intensity of the spectrum attributed to first quantum dot 210' may change with the shielding characteristics of Faraday cage 206.

In some embodiments, Faraday cage 206 is configured to block at least one of the excitation radiation to first structure 210 or the emitted radiation from first structure 210. More specifically, Faraday cage 206 may be configured to block both the excitation radiation to first structure 210 and the emitted radiation from first structure 210.

Figure 2C:
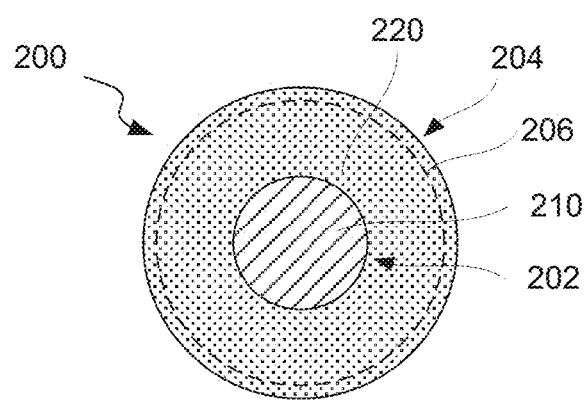
FIG. 2C is a schematic representation another example of a hybrid spectral sensor, in accordance with some embodiments.

In some embodiments, Faraday cage 206 is formed by fully encapsulating first structure 210 with at least one second structure 220 as, for example, shown in FIGS. 2B and 2C. This full encapsulation may be achieved prior to incorporating hybrid spectral sensor 200 into part 300. This level of encapsulation may later change as various forces are applied to hybrid spectral sensor 200 while hybrid spectral sensor 200 is in part 300. To achieve full encapsulation, second structures 220 may block any direct radiation path to and from at least one first structure 210 of hybrid spectral sensor 200.

In some embodiments, first structure 210 is encapsulated by multiple second structures 220 as, for example, shown in FIG. 2B. This type of hybrid spectral sensor 200 may be formed by previously formed second structures 220. For example, second structures may be aggregated around at least one first structure 210. Alternatively, only one second structure 220 form an encapsulating shell around first structure 210 as, for example, shown in FIG. 2C. For example, this single second structure 220 may be formed around first structure 210.

In some embodiments, encapsulating first structure 210 with at least one second structure 220 comprises plasma ionic aggregation. Specifically, plasma-ionic conduction and relaxation properties of the conductive material may server as a basis of the quantum dot development.

After encapsulating first structure 210 with at least one second structure 220 (during operation 110), first structure 210 may be cohesively bonded to at least one second structure 220. This cohesive bonding ensures that Faraday cage 206 retains its characteristics during handling of hybrid spectral sensor 200 and, in some embodiments, during incorporation of hybrid spectral sensor 200 into part 300 as further described below.

To achieve cohesive bonding, first structures 210 and second structures 220 may have functionalized surfaces. Specifically, as shown in FIG. 2B, first structures 210 may have first interacting portion 214, which is in some embodiments, encloses first emitting portion 212. First emitting portion 212 may be responsible for emitting a particular spectrum in response to being exposed to the excitation radiation. First interfacing portion 214 may be transparent to the excitation and emitted radiations and may be specifically configured to form cohesive bonds with second structures 220. Second structures 220 may have second interacting portion 224, which is in some embodiments, encloses second blocking portion 222, as shown in FIG. 2B. Second blocking portion 222 may be responsible for blocking excitation radiation and/or emitted radiation. Second interfacing portion 224 may be specifically configured to form cohesive bonds with first structures 210. Furthermore, second interfacing portion 224 may be configured to bond with component 302 of part 300, such as an adhesive as, for example, shown in FIG. 4A.

Method 100 may proceed with incorporating hybrid spectral sensor 200 into part 300 (refer to block 120 in FIG. 1). In some embodiments, hybrid spectral sensor 200 may be introduced into one component 302 of part 300 prior to forming part 300. For example, hybrid spectral sensor 200 may be introduced into one component 302 of part 300, e.g., mixed into an adhesive 302 used to form a bondline, layup, or the like. Hybrid spectral sensor 200 may be also introduced into individual plies 312a and 312b of layup 310 and/or other components used to form part 310 as, for example, shown in FIG. 3B.

In some embodiments, a concentration of hybrid spectral sensors 200 in part 300 may be less than 1 g/cm$^3$ or, more specifically, less than 0.3 g/cm$^3$ or even less than 0.1 g/cm$^3$. At such low concentrations, hybrid spectral sensors 200 do not impact performance of part 300 while still provide the emitted radiation spectrum of a sufficient intensity.

Figure 3A:
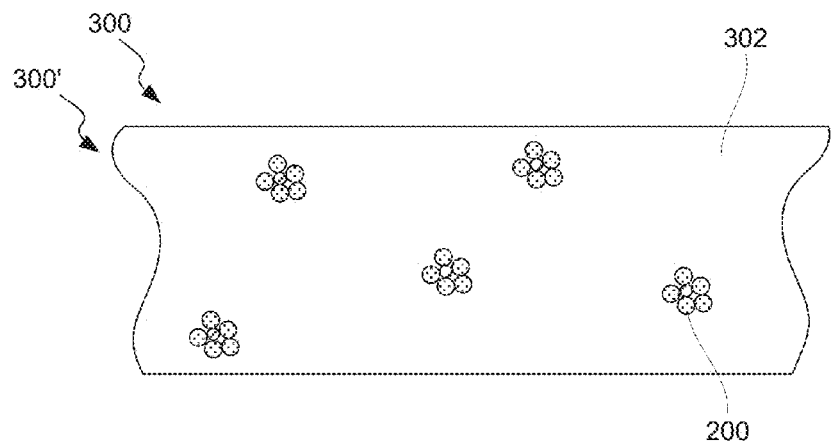
FIG. 3A is a schematic representation a part having hybrid spectral sensors incorporated within, in accordance with some embodiments.
Figure 3B:
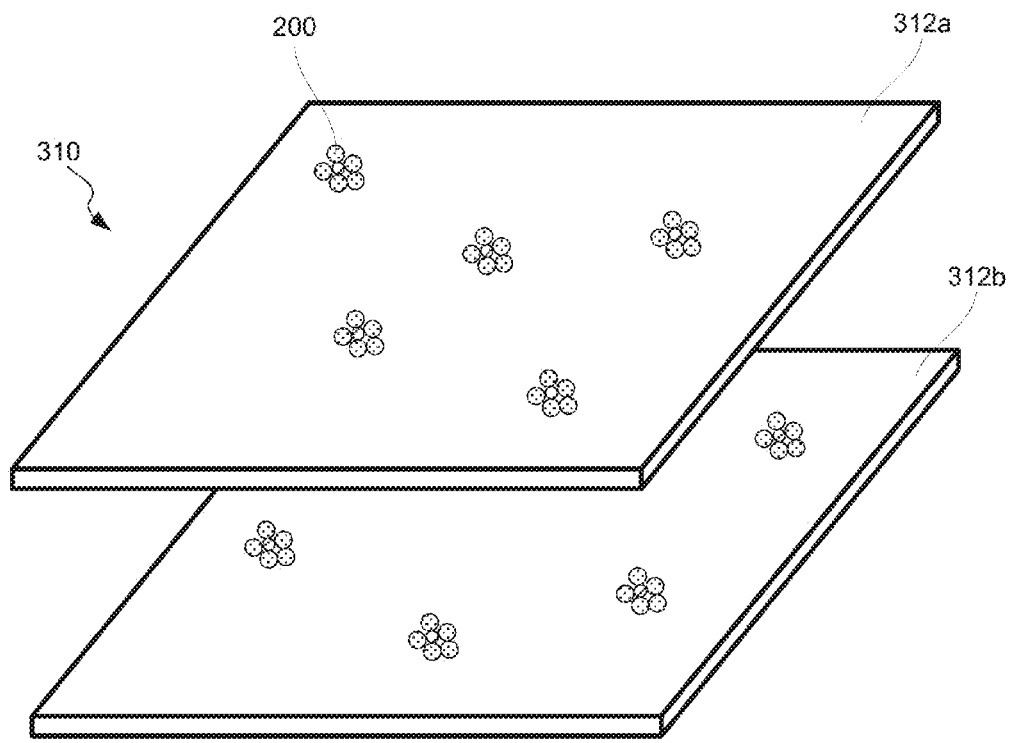
FIG. 3B is a schematic representation a layup having hybrid spectral sensors, the layup used to form a composite part, in accordance with some embodiments.
Figure 3C:
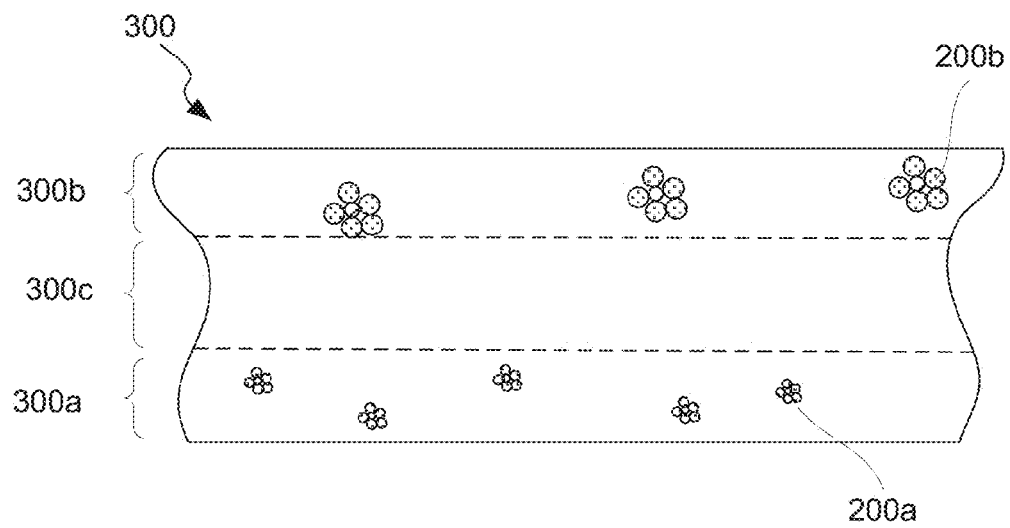
FIG. 3C is a schematic representation another part having two different types of hybrid spectral sensors incorporated within, in accordance with some embodiments.

FIG. 3A is a schematic illustration of hybrid spectral sensors 200 distributed within part 300. In some embodiments, hybrid spectral sensors 200 may be evenly distributed within part 300. Alternatively, hybrid spectral sensors 200 may be concentrated at a surface of part 300 or interface of part 300 where monitoring is desired. Furthermore, different types of hybrid spectral sensors 200a and 200b may be positioned in different portions 300a and 300b of part 300 to differentiate structural changes of different portions 300a and 330b. For example, FIG. 3C illustrate hybrid spectral sensors 200a within first portion 300a of part 300 and hybrid spectral sensors 200b within second portion 300b of part 300. In some embodiments, another portion 300c of part 300 may be free from hybrid spectral sensors. Specifically, hybrid spectral sensors 200a may be contained within first portion 300a, while hybrid spectral sensors 200b may be contained within second portion 300b. Hybrid spectral sensors 200a and hybrid spectral sensors 200b may be of different types and may have different spectral response.

Figure 4A:
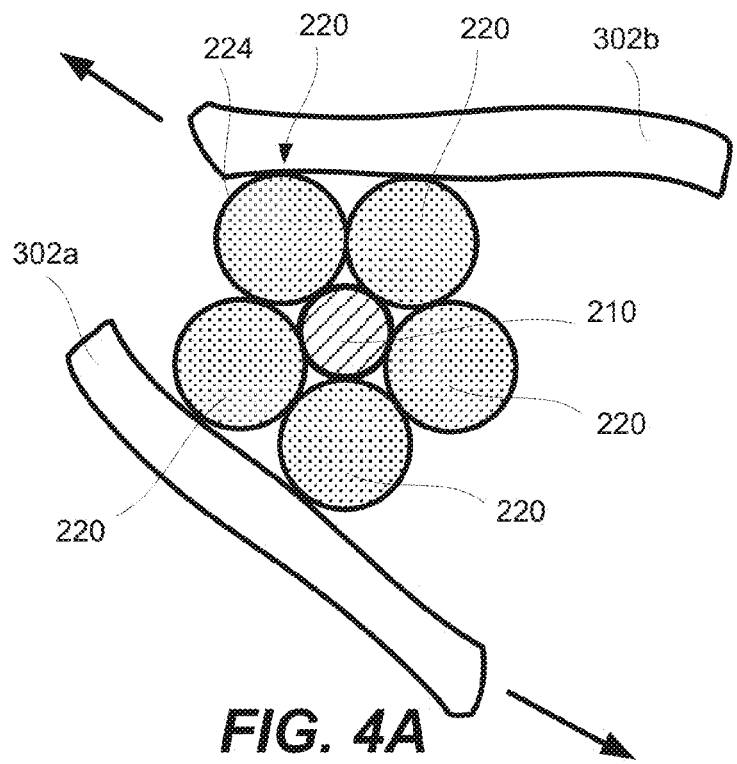
FIGS. 4A-4B are schematic representations of the same hybrid spectral sensor bonded to a part component at various stages during processing and/or us of the part, in accordance with some embodiments.
Figure 4B:
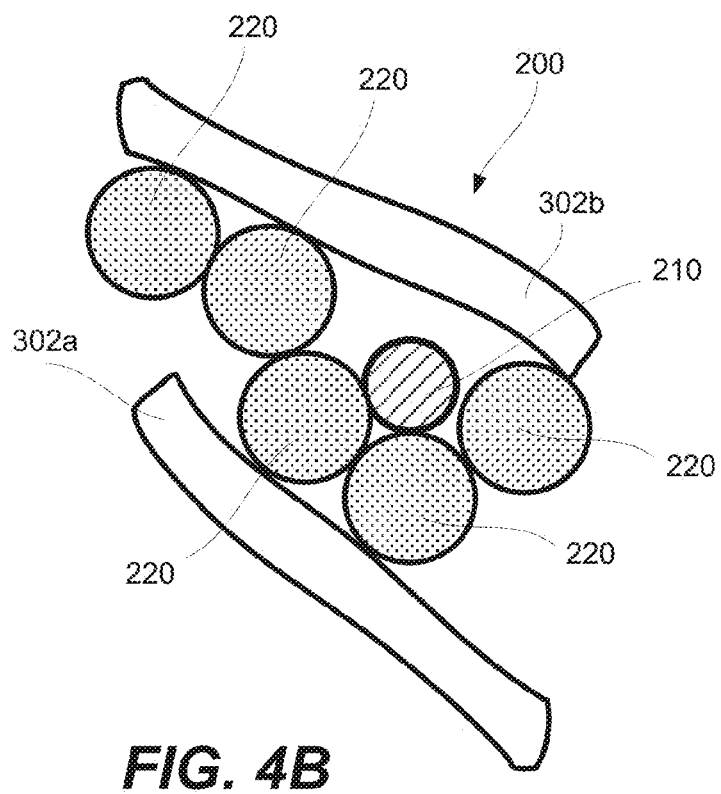

After hybrid spectral sensor 200 is incorporated into part 300, at least one second structure 220 bonds to component 302 of part 300, such as an adhesive. In some embodiments, different second structures 220 of the same hybrid spectral sensors 200 may be bonded to different portions 302a and 302b of component 302 as, for example, schematically shown in FIG. 4A. This bonding ensures that when different portions 302a and 302b of component 302 move with respect to each other, shielding characteristics of Faraday cage 206 may change. For example, applying an excessive load to part 300 may shift portions 302a and 302b relative to each other. Shifting may also occur as a result of other operations and stresses applied to part 300. FIG. 4A illustrates an example of hybrid spectral sensor 200 in which Faraday cage 206 is relatively complete. On the other hand, FIG. 4B illustrates the same hybrid spectral sensor 200 at a different state where first structure 210 is only partially blocked by second structures 220 and some emitted radiation produce by first structure 210 may escape from hybrid spectral sensor 200.

Figure 8A:
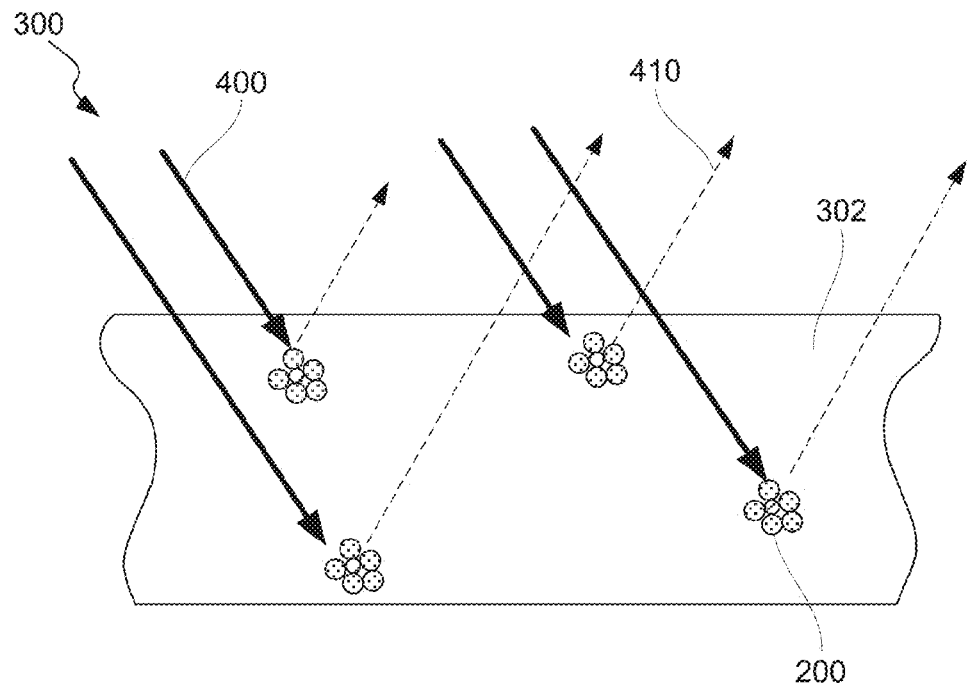
FIGS. 8A-8B are schematic representations of the same part having different configurations of hybrid spectral sensors during exposure of the part to the excitation radiation, in accordance with some embodiments.
Figure 8B:
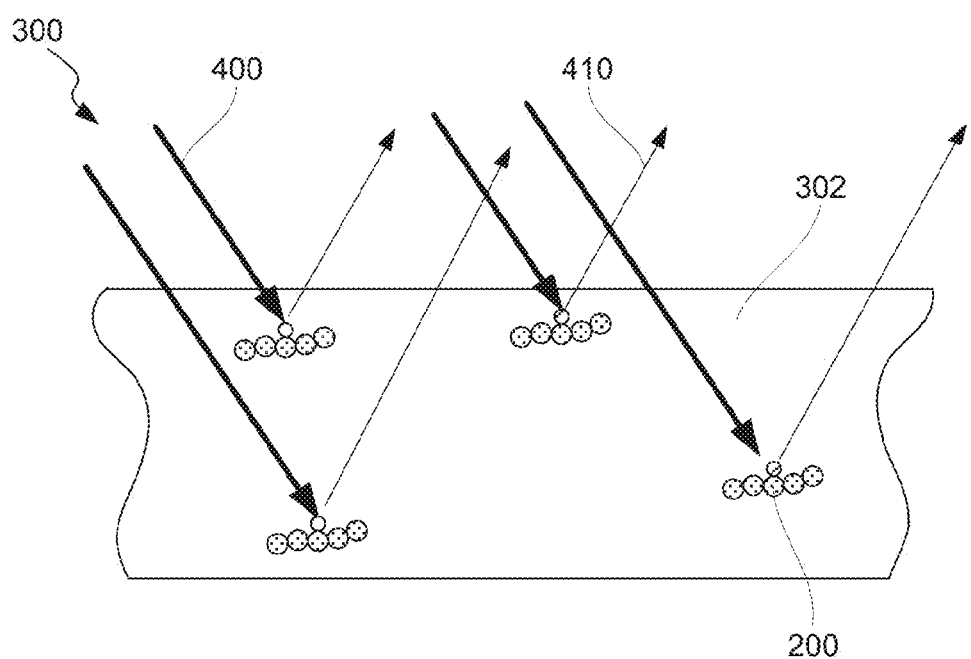

Method 100 may comprise exposing part 300 to excitation radiation 400 (refer to block 140 in FIG. 1 and FIGS. 8A and 8B). Excitation radiation 400 may be specifically tuned to first structures 210 and second structures 220 of hybrid spectral sensors 200 such that a response from first structures 210 is detectable if these first structures 210 are at least partially exposed. In other words, when Faraday cage 206 has some openings, excitation radiation 400 may reach first structures 210 and emitted radiation 410 may escape beyond the boundary of Faraday cage 206. For example, FIG. 8A illustrates part 300 including hybrid spectral sensor 200 having complete Faraday cages (similar to examples of hybrid spectral sensor 200 shown in FIG. 5B or 6A). Very little if any emitted radiation 410 is attributed to the first structures of these hybrid spectral sensors 200. As such, emitted radiation 410 is shown with dashed lines in this figure. On the other hand, FIG. 8B illustrates part 300 including hybrid spectral sensor 200 having only partial complete Faraday cages (similar to examples of hybrid spectral sensor 200 shown in FIG. 5C or 6C). A substantial portion of emitted radiation 410 (in some embodiments, all of emitted radiation) is attributed to the first structures of these hybrid spectral sensors 200.

In some embodiments, excitation radiation 400 may be provided by a microwave amplification by stimulated emission of radiation (MASER) device or a terahertz excitation device. Excitation radiation 400 may activate at least first structures (e.g., inner quantum dots) when these structures are not shielded by the second structures.

Figure 7A:
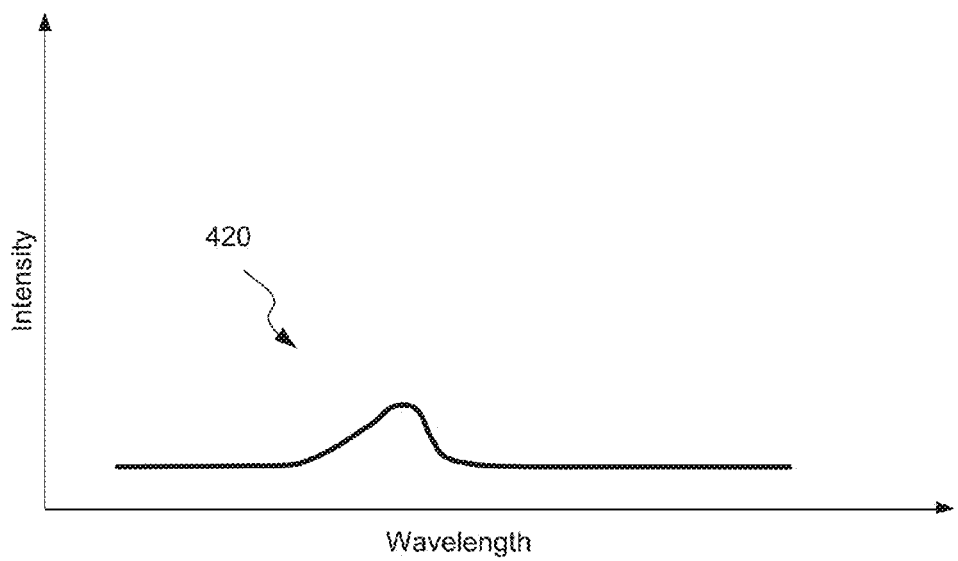
FIGS. 7A and 7B are examples of spectral responses of the same hybrid spectral sensors at different states, in accordance with some embodiments.
Figure 7B:
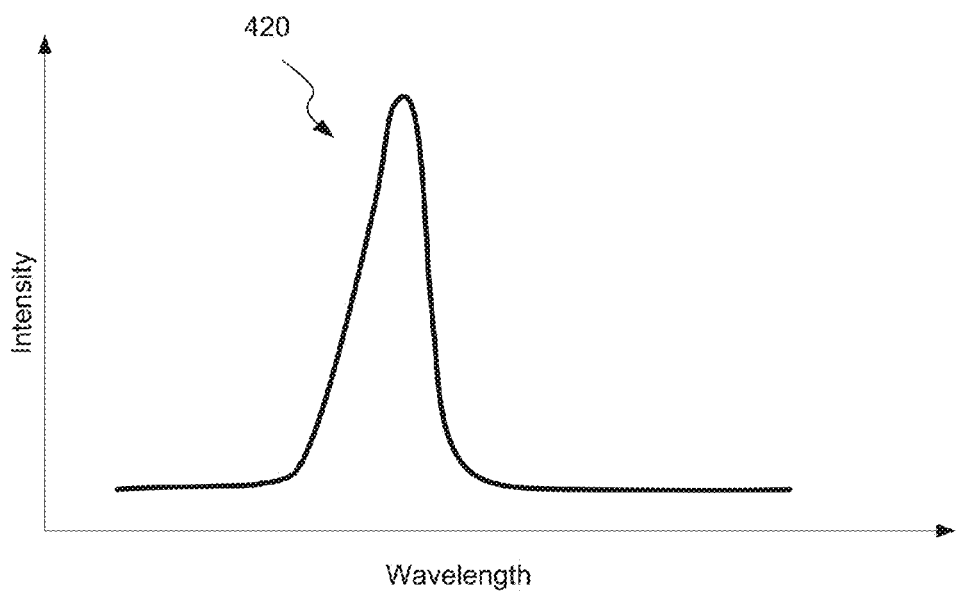

Emitted radiation 410 may be detected, measured, and stored using various optical detection techniques. Method 100 may comprise analyzing spectrum 420 of emitted radiation 410 (refer to block 150 in FIG. 1). Depending on the shielding effectiveness of Faraday cage 206 at the time of exposing part 300 to excitation radiation 400, spectrum 420 of emitted radiation 410 may change as schematically shown in FIGS. 7A and 7B. A lookup table or a calibration spectrum may be used to analyze this emitted radiation spectrum 420 and, for example to correlate of spectrum 420 to bondline characteristics. In general, spectrum 420 may be analyzed to determine inconsistencies in part 300.

Spectrum 420 of emitted radiation 410 depends on openings in Faraday cage 206 of hybrid spectral sensors 200 in part 300. In other words, spectrum 420 of emitted radiation 410 depends on the encapsulation level of first structure 210 by at least one second structure 220. This level of encapsulation may change as part 300 is further processes after incorporating hybrid spectral sensor 200 into part 300 and/or otherwise used e.g., during operation.

FIG. 5A is a schematic three-dimensional representation of hybrid spectral sensor 200 having first structure 210 encapsulated by multiple second structures 220. Since first structure 210 is blocked by second structures 220, first structure 210 is shown with a dotted line. Line A-A corresponding to a cross-section schematically shown in FIG. 5B, which is a two-dimensional representation of hybrid spectral sensor 200 illustrating first structure 210 encapsulated by second structures 220. FIGS. 5C-5D are schematic two-dimensional representation of the same hybrid spectral sensor 200 having different encapsulation levels of first structure 210 by at least one second structure 220. One having ordinary skills in the art would understand that while FIGS. 5B-5D provide two-dimensional representation of hybrid spectral sensors 200, these sensors are three-dimensional structures and shielding may be provided in all three dimensions.

As noted above, while this example shows a particular number of second structures 220 encapsulating a single first structure 210, any number of first structures 210 and any number of second structures 220 may be used in the same hybrid spectral sensor 200. Returning to the example illustrated in FIGS. 5A and 5B, second structures 220 form complete shell 204 around core 202 formed by first structure 210. The boundaries of Faraday cage 206 are identified with a dashed line 206. This example may represent hybrid spectral sensor 200 after its being formed.

After hybrid spectral sensor 200 is incorporated into part 300 and after subject part 300 to various processing operations, orientations of at least some second structures 220 relative to first structure 210 may change as schematically shown in FIGS. 5C and 5D. Specifically, FIG. 5C illustrates hybrid spectral sensor 200 where only about one half of first structure 210 is shielded by second structures. FIG. 5D illustrates an example of hybrid spectral sensor 200 where first structure is shielded even less than the example shown in FIG. 5C. FIG. 5E is a schematic three-dimensional representation of hybrid spectral sensor 200 in the state represented by FIG. 5D.

Figure 6A:
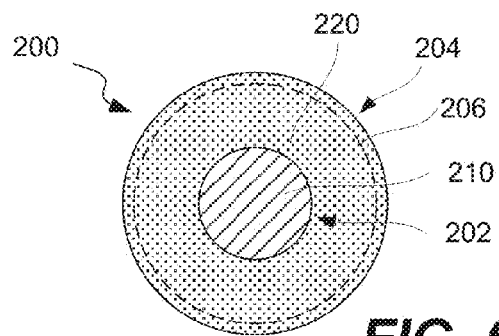
FIGS. 6A-6D are schematic representations of another example of a hybrid spectral sensor at different states.
Figure 6B:
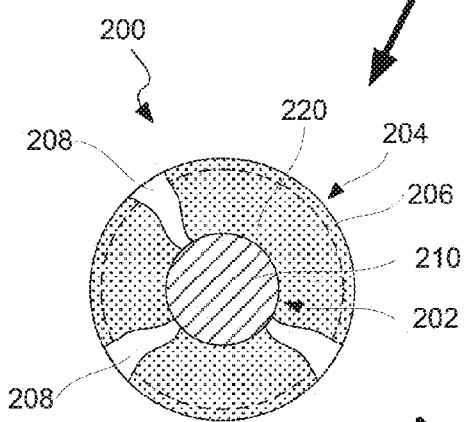
Figure 6C:
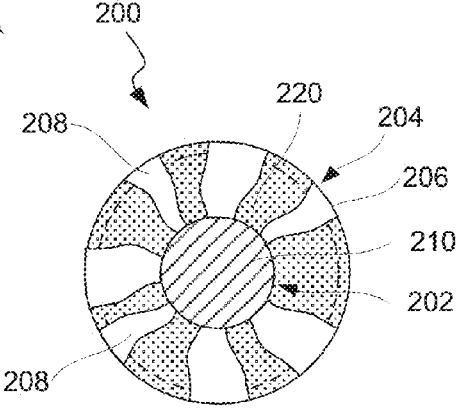

FIGS. 6A-6C are schematic illustrations of another example of hybrid spectral sensor 200 having different encapsulation levels of first structure 210 by at least one second structure 220. In this example, one second structure 220 forms either complete shell 204 as shown in FIG. 6A or partial shell 204 as shown in FIGS. 6B and 6C. Partial shells 204 in FIGS. 6B and 6C still form Faraday cages 206 that have openings 208. For example, second structure 220 may be cracking while subjected part 300 is being subjected to various processing and/or operations.

Figure 6D:
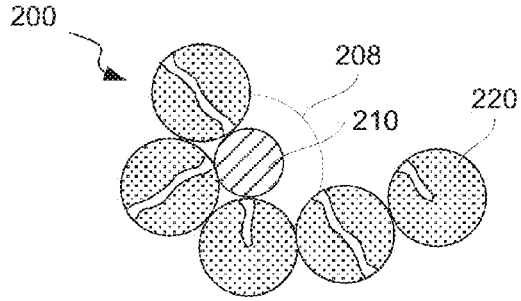

It should be noted that changes to shell 204 shown in FIGS. 5A-5E and FIGS. 6A-6C are not necessarily alternative embodiments. These types of changes may occur simultaneously as, for example, is schematically shown in FIG. 6D illustrating changes in both orientation of second structures 220 and encapsulation ability of each individual structure.

The portion of emitted radiation 410 attributable to first structures 210 is distinguishable from the portion of emitted radiation 410 attributable to at least one second structure 220. As such, the same hybrid spectral sensor 200 having different encapsulation levels of first structure 210 (at different processing/operation stages) will produce different emitted spectrum as schematically shown in FIGS. 7A and 7B. In some embodiments, the at least one second structure 220 does not produce any detectable emitted radiation 410 when exposure to the emitted radiation.

Method 100 may further comprise processing part 300 (refer to block 160 in FIG. 1). This processing is performed after incorporating hybrid spectral sensors 200 into part 300. As such, some changes to part 300 that occur during this processing may be registered by hybrid spectral sensors 200 in part 300.

In some embodiments, part 300 is composite part 300′. In these embodiments, the processing may involve curing the part 300, which is an optional operation. If hybrid spectral sensor 200 is incorporated into part 300 prior to curing part 300, hybrid spectral sensors 200 may be used for monitoring the curing operation. Furthermore, hybrid spectral sensors 200 for monitoring various pre-curing operations (e.g., incorporated into the resin prior or while combining the resins with fibers) and/or various post-curing processes as further described below.

In some embodiments, processing part 300 may be performed after exposing part 300 to excitation radiation 400 during, for example, operation 140. This exposure prior to processing may be used to generate a control spectrum. In some embodiments, exposing part 300 may be repeated after processing as illustrated by decision block 170 in FIG. 1. Specifically, part 300 may be exposed to an additional excitation radiation after completing the processing. The additional excitation radiation may be the same as the excitation radiation used prior to processing. Method 100 may then proceed with analyzing the spectrum of an additional emitted radiation produced when part 300 is exposed to the additional excitation radiation. Method 100 may further comprise comparing the spectrum of the emitted radiation (e.g., the pre-processing/control spectrum) to the spectrum of the additional emitted radiation (e.g., the post-processing spectrum) as shown by block 152 in FIG. 1.

In some embodiments, processing performed on part 300 (after incorporating hybrid spectral sensor 200 into part 300) may comprise bondline curing (block 162), which may involve cold bonding process, UV curing and bonding, and/or microwave curing.

Examples of Aircraft and Methods of Fabricating and Operation Aircraft

Figure 9:
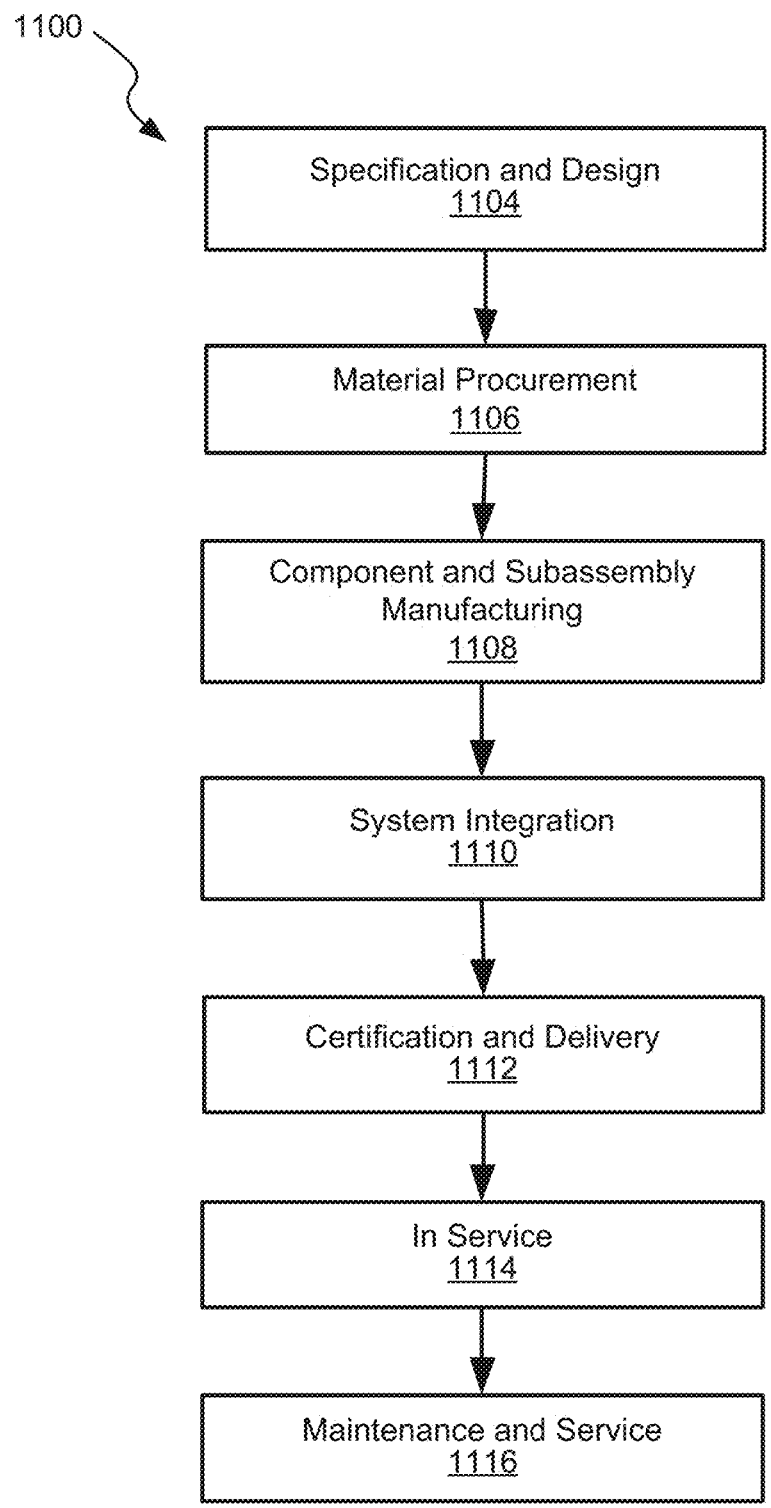
FIG. 9 is a block diagram of aircraft production and service methodology that may utilize end effectors described herein.
Figure 10:
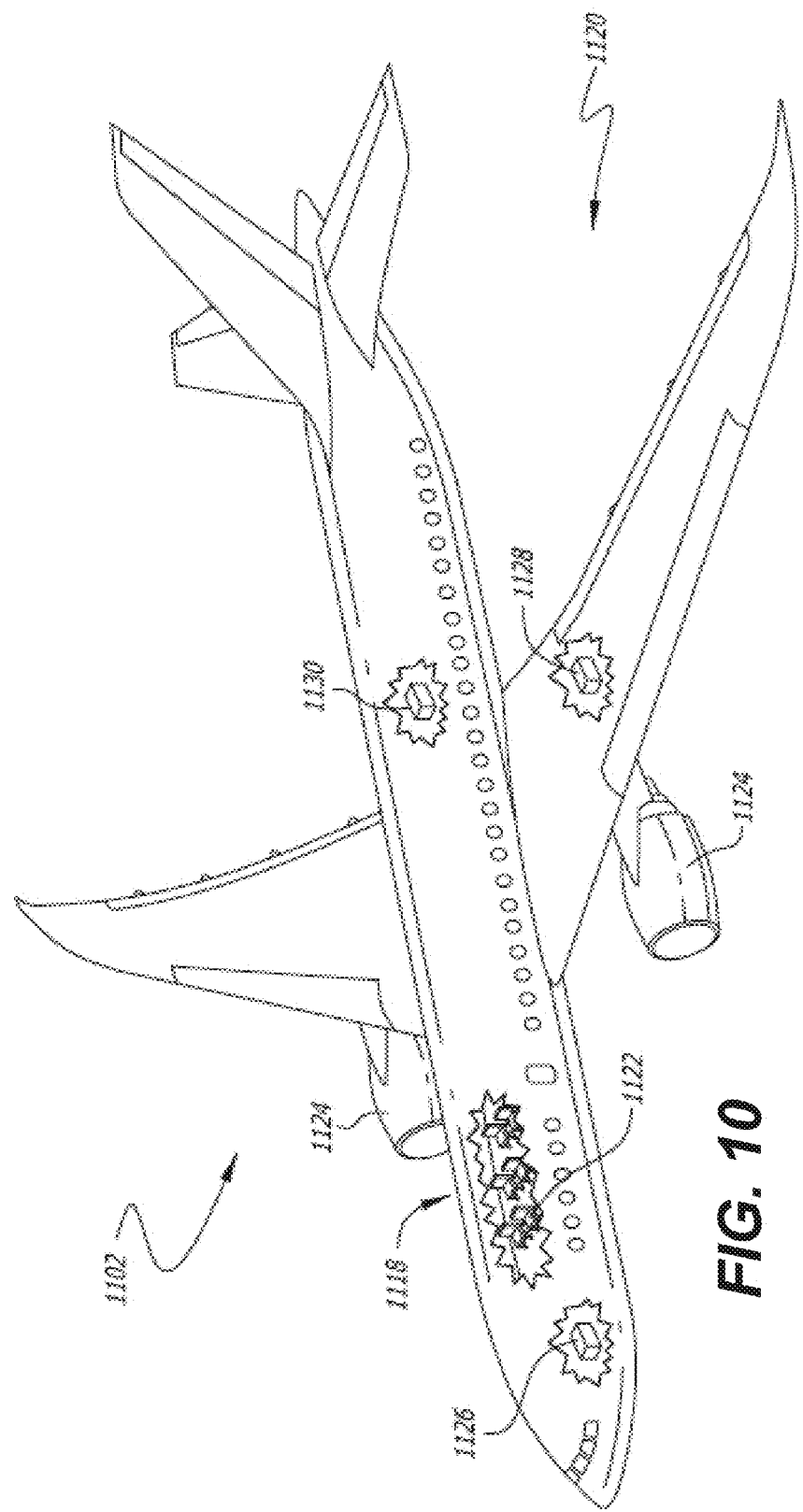
FIG. 10 is a schematic illustration of an aircraft that may include composite structures described herein.

Examples of the present disclosure may be described in the context of aircraft manufacturing and service method 1100 as shown in FIG. 9 and aircraft 1102 as shown in FIG. 10. During pre-production, method 1100 may include specification and design (block 1104) of aircraft 1102 and material procurement (block 1106). During production, component and subassembly manufacturing (block 1108) and system integration (block 1110) of aircraft 1102 may take place. Hybrid spectral sensors 200 may be used as a part of any of these operations. For example, hybrid spectral sensors 200 may be introduced into different parts of aircraft 1102 during part fabrication and scanned during component and subassembly manufacturing (block 1108) and system integration (block 1110). Thereafter, aircraft 1102 may go through certification and delivery (block 1112) to be placed in service (block 1114). While in service, aircraft 1102 may be scheduled for routine maintenance and service (block 1116). Routine maintenance and service may include modification, reconfiguration, refurbishment, etc. of one or more systems of aircraft 1102. Hybrid spectral sensors 200 may be introduced into part 300 and/or may be scanned during material procurement (block 1106), component and subassembly manufacturing (block 1108) and system integration (block 1110), certification and delivery (block 1112), service (block 1114), and/or routine maintenance and service (block 1116).

Each of the processes of method 1100 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 10, aircraft 1102 produced by method 1100 may include airframe 1118 with a plurality of high-level systems 1120 and interior 1122. Examples of high-level systems 1120 include one or more of propulsion system 1124, electrical system 1126, hydraulic system 1128, and environmental system 1130. Part 300 having hybrid spectral sensors 200 may be used in either one of airframe 1118, the plurality of high-level systems 1120, and interior 1122. Any number of other systems may be included. Although an aerospace example is shown, the principles disclosed herein may be applied to other industries, such as the automotive industry. Accordingly, in addition to aircraft 1102, the principles disclosed herein may apply to other vehicles, e.g., land vehicles, marine vehicles, space vehicles, etc.

Apparatus(es) and method(s) shown or described herein may be employed during any one or more of the stages of method 1100. For example, components or subassemblies corresponding to component and subassembly manufacturing (block 1108) may be fabricated or manufactured in a manner similar to components or subassemblies produced while aircraft 1102 is in service (block 1114). Also, one or more examples of the apparatus(es), method(s), or combination thereof may be utilized during production stages (block 1108 and block 1110), for example, by substantially expediting assembly of or reducing the cost of aircraft 1102. Similarly, one or more examples of the apparatus or method realizations, or a combination thereof, may be utilized, for example and without limitation, while aircraft 1102 is in service (block 1114) and/or during maintenance and service (block 1116).

CONCLUSION

Different examples of the apparatus(es) and method(s) disclosed herein include a variety of components, features, and functionalities. It should be understood that the various examples of the apparatus(es) and method(s) disclosed herein may include any of the components, features, and functionalities of any of the other examples of the apparatus(es) and method(s) disclosed herein in any combination, and all of such possibilities are intended to be within the spirit and scope of the present disclosure.

Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples provided in the present disclosure.

What is claimed is:

1. A method comprising:
forming a Faraday cage around a first structure by at least partially encapsulating the first structure with at least one second structure to form a hybrid spectral sensor, wherein the first structure is a first quantum dot, wherein the at least one second structure is at least one second quantum dot different from the first quantum dot; and
incorporating the hybrid spectral sensor into a part, such that changes in the structure of the part cause a change in the structure of the Faraday cage.

2. The method of claim 1, wherein the at least one second quantum dot is bonded to a component of the part after the hybrid spectral sensor is incorporated into the part.

3. The method of claim 2, wherein the component of the part is an adhesive.

4. The method of claim 1, wherein, after encapsulating the first quantum dot with the at least one second quantum dot, the first quantum dot is cohesively bonded to the at least one second quantum dot.

5. The method of claim 1, wherein the part is a composite part.

6. The method of claim 5, further comprising curing the part, wherein the hybrid spectral sensor is incorporated into the part prior to curing the part.

7. The method of claim 1, further comprising:
exposing the part to an excitation radiation; and
analyzing spectrum of an emitted radiation from the part to determine inconsistencies in the part.

8. The method of claim 7, wherein the spectrum of the emitted radiation depends on an opening in the Faraday cage of the hybrid spectral sensor.

9. The method of claim 7, wherein a portion of the emitted radiation attributable to the first quantum dot is distinguishable from a portion of the emitted radiation attributable to the at least one second quantum dot.

10. The method of claim 7, further comprises processing the part,
wherein processing is performed prior to exposing the part to the excitation radiation, and
wherein processing is performed after incorporating the hybrid spectral sensor into the part.

11. The method of claim 10, wherein the processing comprises bondline curing.

12. The method of claim 7, further comprising:
processing the part, wherein processing is performed after exposing the part to the excitation radiation;
exposing the part to an additional excitation radiation after completing the processing; and
analyzing spectrum of an additional emitted radiation.

13. The method of claim 1, wherein the Faraday cage is formed by fully encapsulating the first quantum dot with the at least one second quantum dot.

14. The method of claim 1, wherein the first structure is encapsulated by multiple second structures comprising the at least one second quantum dot.

15. The method of claim 1, wherein the at least one second quantum dot form an encapsulating shell around the first quantum dot.

16. A method of testing a part, the method comprising:
forming one or more hybrid spectral sensors;
forming each hybrid spectral sensor as a Faraday cage by at least partially encapsulating a first structure with at least one second structure,
wherein the first structure is a first quantum dot,
wherein the at least one second structure is at least one second quantum dot different from the first quantum dot;
incorporating the one or more hybrid spectral sensors into the part;
processing the part;
exposing the part to an excitation radiation; and
analyzing spectrum of an emitted radiation from the one or more hybrid spectral sensors to determine inconsistencies in the part.

17. The method of claim 16, wherein changes to the structure of the part that occur during processing cause changes in the structure of the Faraday cage of one or more hybrid spectral sensors.

18. A hybrid spectral sensor comprising:
a first structure; and
a Faraday cage around a first structure formed by at least partially encapsulating the first structure with at least one second structure,
wherein the first structure is a first quantum dot,
wherein the at least one second structure is at least one second quantum dot different from the first quantum dot;
wherein the hybrid spectral sensor is incorporated into a part, such that changes to the structure of the part cause a change to the structure of the Faraday cage.

* * * * *